(12) United States Patent
Boeing et al.

(10) Patent No.: US 7,903,859 B2
(45) Date of Patent: Mar. 8, 2011

(54) IMAGE ACQUISITION, ARCHIVING AND RENDERING SYSTEM AND METHOD FOR REPRODUCING IMAGING MODALITY EXAMINATION PARAMETERS USED IN AN INITIAL EXAMINATION FOR USE IN SUBSEQUENT RADIOLOGICAL IMAGING

(75) Inventors: Dieter Boeing, Forchheim (DE); Heinz-Peter Engels, Munich (DE)

(73) Assignee: Siemens Aktiengesellschaft, Munich (DE)

( * ) Notice: Subject to any disclaimer, the term of this patent is extended or adjusted under 35 U.S.C. 154(b) by 308 days.

(21) Appl. No.: 12/134,312

(22) Filed: Jun. 6, 2008

(65) Prior Publication Data
US 2008/0310698 A1 Dec. 18, 2008

(30) Foreign Application Priority Data
Jun. 8, 2007 (DE) .................... 10 2007 026 520

(51) Int. Cl.
*G06K 9/00* (2006.01)
*A61B 5/05* (2006.01)
*A61B 6/00* (2006.01)

(52) U.S. Cl. ................ 382/131; 600/425; 378/21

(58) Field of Classification Search ............ 382/128, 382/129, 130, 131, 132, 133, 134; 378/4, 378/20–27, 205, 901; 600/407, 410, 411, 600/425, 427, 429; 128/915, 916, 920, 922; 250/363.04; 424/9.4
See application file for complete search history.

(56) References Cited

U.S. PATENT DOCUMENTS

| | | | | |
|---|---|---|---|---|
| 4,791,934 A | * | 12/1988 | Brunnett | 600/429 |
| 7,177,453 B2 | * | 2/2007 | Suryanarayanan et al. | 382/128 |
| 7,570,051 B2 | * | 8/2009 | Haider | 324/307 |
| 2002/0049378 A1 | | 4/2002 | Grzeszczuk et al. | |
| 2005/0165294 A1 | | 7/2005 | Weiss | |
| 2006/0239589 A1 | | 10/2006 | Omernick et al. | |
| 2007/0162305 A1 | * | 7/2007 | Miller | 705/2 |

OTHER PUBLICATIONS

"Consistency of Softcopy and Hardcopy: Preliminary Experiences with the new DICOM Extensions for Image Display," Eichelberg et al, Medical Imaging 2000, pp. 97-106 (2000).

* cited by examiner

*Primary Examiner*—Abolfazl Tabatabai
(74) *Attorney, Agent, or Firm*—Schiff Hardin LLP

(57) ABSTRACT

An imaging method and system allow duplicated repetition of a procedure to acquire image data from the interior of the body of a patient and to generate an image of the interior of the body of the patient with an initial imaging modality, that is operated using patient-specific examination parameters to implement a procedure to acquire the image data and generate the image. The patient-specific examination parameters are electronically stored, and are electronically retrieved to implement a duplicate of the aforementioned procedure in an imaging modality-assisted follow-up examination.

27 Claims, 3 Drawing Sheets

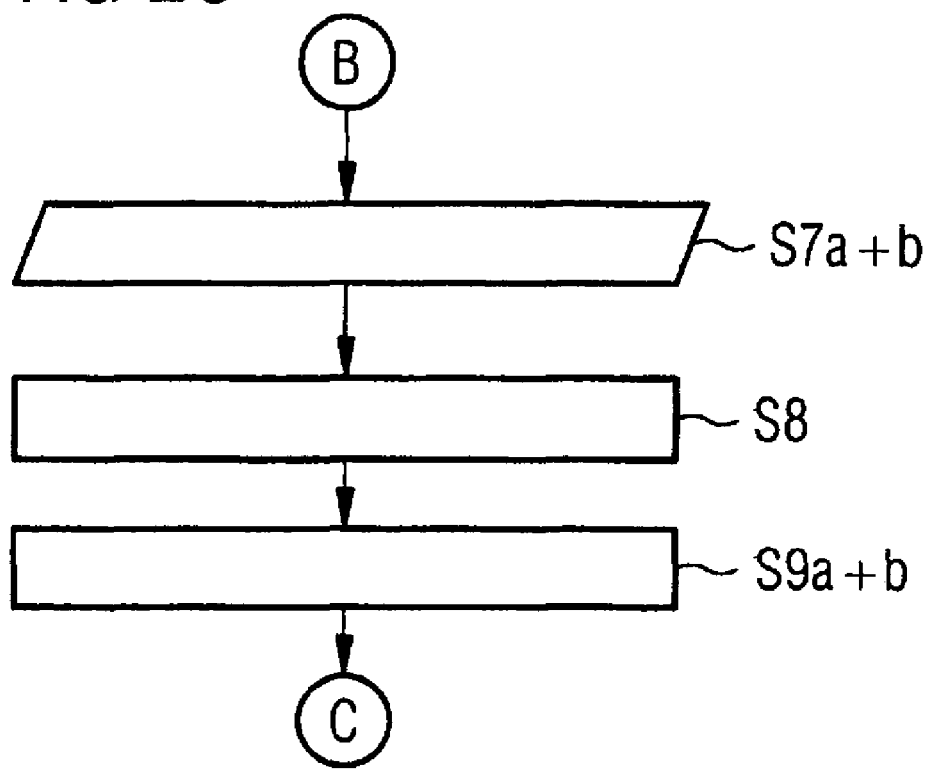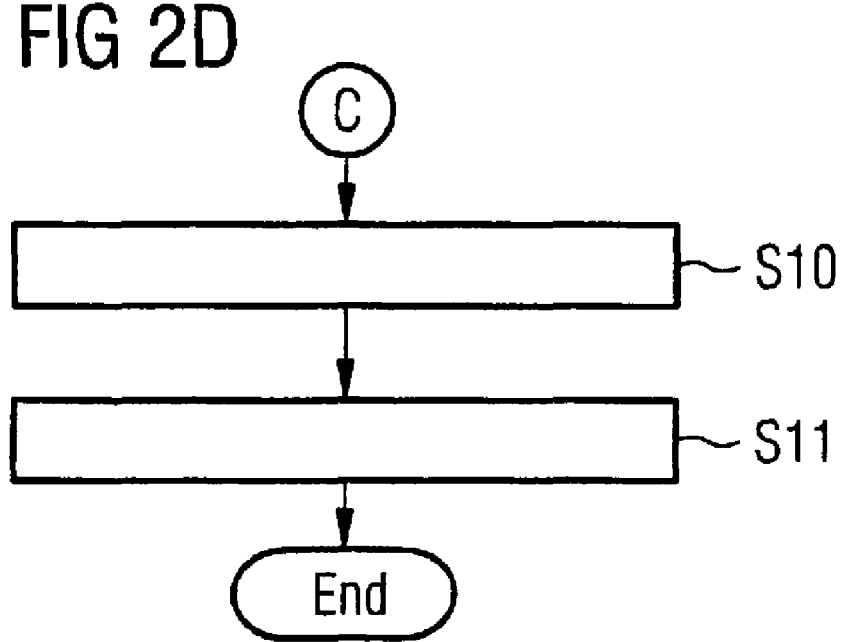

IMAGE ACQUISITION, ARCHIVING AND RENDERING SYSTEM AND METHOD FOR REPRODUCING IMAGING MODALITY EXAMINATION PARAMETERS USED IN AN INITIAL EXAMINATION FOR USE IN SUBSEQUENT RADIOLOGICAL IMAGING

BACKGROUND OF THE INVENTION

1. Field of the Invention

The present invention concerns a CT-assisted or MRT-assisted image acquisition, image archiving and image rendering system for generation, storage, post-processing, retrieval and graphical visualization of computed or magnetic resonance tomography image data that, for example, can be used in the clinical field in the framework of radiological slice image diagnostics as well as in the framework of interventional radiology. The present invention also concerns a method implemented by such a system for reproduction of patient-specific examination parameters of an initial examination implemented by means of computer or magnetic resonance tomography imaging in the framework of CT or MRT follow-up examinations ("follow-ups"), for example in a post-operative tumor examination implemented under slice image monitoring in connection with a histological tissue sample extraction (biopsy) implemented under local anesthesia or a minimally-invasive intervention implemented for tumor treatment.

2. Description of the Prior Art

In the case of certain clinical situations, in particular in the field of tumor diseases, today monitoring examinations ("check-ups") are implemented at predetermined time intervals by means of slice image diagnostics. In particular modern radiological imaging methods such as, for example, computed tomography (CT), positron emission tomography (PET) in combination with computer tomography or magnetic resonance tomography (MRT) are used. By means of these regularly conducted check-ups it is possible to register changes of the clinical picture of a patient that are externally not visible. In the event that the cancer reappears in a tumor patient or a new, malignant tumor develops from metastases, these can be promptly detected and be operatively treated as quickly as possible using a minimally-invasive procedure or conducted under local anesthesia. If the medically recommended post-operative tumor examinations are consistently administered by the patient and the indicated therapies are conducted, in many cases a cure, life extension or at least maintenance of the quality of life are real possibilities.

A predetermined standard examination protocol is typically loaded to plan the initial examination, in which standard examination protocol examination, acquisition and 2D/3D image rendering parameters (reconstruction parameters) are then manually adapted by a radiologist conducting the examination to a patient to be examined by means of CT, PET-CT or MRT.

In order to be able to compare image data of an initial examination implemented by means of CT-, PET-CT- or MRT-assisted imaging (which image data are presented in the form of axial slice exposures or in the form of reconstructed 2D projections or 3D views of areas to be examined inside the body of a patient) with those of subsequent monitoring examinations of the patient (likewise conducted under CT or MRT imaging) as well as possible, in the ideal case the same acquisition parameters as in the initial examination should be used in the follow-up examinations. Moreover, the slice exposures displayed on the screen, reconstructed 2D projections or 3D views of tissue regions, organs, anatomical subjects or pathological structures that are to be examined (such as tumors, metastases, hematomas, abscesses etc., for example) inside the body of the patient should be reconstructed with the same 2D or 3D reconstruction parameters as in the initial examination. Conventionally, all parameters from the initial examination must be input manually into the CT or MRT system by a radiologist conducting the initial and follow-up examination.

Since in present-day radiological imaging, image archiving and image processing systems it is not possible to store all parameters that were set in an initial examination of a patient implemented by means of CT, PET-CT or MRT, at present there exists no possibility to precisely set these parameters again in subsequent CT-, PET-CT- or MRT-based follow-up examinations so that the examination results of the radiological initial examination can be exactly reproduced. For the same reasons deviations between the image data of this initial examination and the image data of a radiological follow-up examination that show an improvement or worsening of a pathological state diagnosed in the framework of the initial examination cannot be evaluated under the same acquisition and reconstruction conditions.

A further problem of present CT-assisted or MRT-assisted imaging, image archiving and image processing systems is that the position occupied by a patient on the examination table of a CT or MRT apparatus (i.e. the patient position) in an initial examination cannot be exactly repeated upon implementation of a follow-up examination, i.e. with the same position and angle coordinates relative to a three-dimensional Cartesian coordinate system I (patient coordinate system) which is spanned by the longitudinal axis z of the body of the patient and two direction vectors proceeding orthogonal to one another in the x-direction (transverse-horizontal) or in the y-direction (transverse-vertical). These direction vectors are direction vectors of a slice plane $E_{xy}$ normal (transverse) relative to the longitudinal axis of the body, with a suitably established point A indicating the position of the coordinate origin in the patient coordinate system. This leads to the situation that two different inertial systems I and I' must be differentiated, i.e. a three-dimensional Cartesian coordinate system I' defined by the spatial position of an examination table movable relative to the CT or MRT apparatus in the feed direction z, with a coordinate origin O' as well as three axes x', y' and z' orthogonal to one another (table coordinate system), and the patient coordinate system I defined by the position of the patient relative to this table coordinate system, with a coordinate origin O as well as the three aforementioned axes x, y and z orthogonal to one another. If the patient lies prone on the examination table of the CT or MRT apparatus, the y-axis of the patient coordinate system and the y'-axis of the table coordinate system are parallel to one another and the planes spanned by the x-axis and z-axis of the patient coordinate system, and by the x'-axis and z'-axis of the table coordinate system, are coplanar with one another. Since, upon implementation of a CT or MRT examination, the patient is not always able to exactly occupy the same orientation and position as in a prior examination implemented by means of computed tomography or magnetic resonance tomography imaging (even with repeated correction of his or her resting position occurring at the instruction of a radiologist in advance of the radiological examination), it must be noted that the position offset and angle offset coordinates (which are required for an initial CT-assisted or MRT-assisted examination in order to convert between both coordinate systems) are generally not correlated with the corresponding position offset and angle offset coordinates in subsequent examinations conducted in the framework of computed tomography or magnetic resonance tomography imaging processes. For this reason, all position and angle coordinates that are used to define the x-, y- and z-positions and the orientation in the φ-direction and the or θ-direction of a 2D or 3D reconstruction generated in the framework of a 2D or 3D post-processing by means of multiplanar reformation, maximum intensity projection or volume rendering technique, are always related to the table coordinate system. However, all of these position and angle coordinates must actually relate to the patient coordinate system in order to be able to achieve exactly reproducible image data independent of the patient position in temporally successive examinations.

Since a repetition of the CT-assisted or MRT-assisted imaging process under the same conditions as in an initial examination (with the exact same parameter specifications) of the appertaining patient implemented by means of CT or MRT is presently not possible upon implementation of a radiological follow-up examination, both examinations are typically planned and implemented individually. The parameter settings for the radiological follow-up examination are reestablished starting from the image data generated in the framework of the initial examination and are used for generation of 2D or 3D reconstructions and protocolled data of a scan protocol acquired after conclusion of the scan procedure of this initial examination and stored in a report or, respectively, finding file. This is a relatively time-consuming process that must be manually executed by a radiologist implementing both examinations.

In the planning of the follow-up examination it should be noted that the standard examination protocol used in the framework of the initial examination must be reused, and all information displayed in graphical or text form on the display screen of a monitor terminal connected with the CT or MRT system (which information relate to the setting parameters of the initial examination), such as the acquisition and reconstruction parameters displayed in a display window in the form of image text, for example, must be checked and possibly reconfigured.

Moreover, the spatial orientation of the slices shown in an initial examination in the framework of an MRT-assisted imaging process, nor the spatial orientation of 2D or 3D reconstructions that were generated in the framework of a post-processing process implemented after the initial examination, are not reproducible in commercially available CT and MRT systems. Rather, such information must be estimated on the basis of the respective prior examination and be manually input by the radiologist conducting the examinations, which (apart from the not inconsiderable time expenditure that accumulates over multiple follow-up examinations) is prone to a relatively large imprecision of the image reproduction.

Added to this is the imprecision (described above) ascribed to the non-correlation of the respective position offset and angle offset coordinates of table coordinate system and patient coordinate system in temporally successive CT-assisted or MRT-assisted examinations that have been conducted with different patient positions. The position offset coordinates ($\Delta x$, $\Delta y$ and $\Delta z$) and/or the angle offset coordinates ($\Delta \phi$) with which the two inertial systems I and I' can be converted into one another before implementation of the initial examination, and the corresponding offset coordinates with which the table coordinate system and the patient coordinate system can be brought into relation to one another in advance of a follow-up examination, can be only conditionally approximated to one another (i.e. brought into correlation with one another). For example, this can occur when the patient is lying in extended dorsal, prone or side position on the examination table of a CT or MRT apparatus, and is instructed to change his/her recumbent position until he/she comes to lie with a punctiform spot $P(x_0, y_0, z_0)$ on his/her body surface (for example at a specific point in the cranial region of the calvaria) exactly on an established punctiform spot $P'(x_0', y_0', z_0')$ on the top of the examination table. This leads to the situation that the position offset and angle offset coordinates in the respective follow-up examination exhibit the same values as in the initial examination. For this purpose it is required that the appertaining body point P be detected with the use of a laser sighting device in each examination before implementation of a scan process, and the table position is recalibrated so that the two aforementioned punctiform spots P and P' come into congruence. By suitable establishment of the positions of these two punctiform spots and consolidation of the direction of the table feed (axial direction) with the z-axis of the patient coordinate system it can also be ensured that the table and patient coordinate systems coincide. This method is naturally very strongly dependent on how precisely the radiologist conducting the examinations sets the position of the examination table. A subsequent correction of the table position given a position change of the patient by $\Delta x$ and/or $\Delta z$ in the ±x-direction and ±z-direction (i.e. in the transverse-horizontal and axial directions) or given a rotation of his/her position by $\Delta \phi$ in the ±φ-direction (i.e. via rotation on an axis perpendicular to the x-z-plane of the patient coordinate system, which x-z-plane is parallel to the table plate plane) is not possible during the implementation of a CT, PET-CT or MRT scan process.

SUMMARY OF THE INVENTION

An object of the present invention is to allow image data of slice exposures acquired in the framework of an initial examination by means of CT-assisted or MRT-assisted imaging and/or 2D projections or, respectively, 3D views of specific tissue regions, internal organs, anatomical subjects or, respectively, pathological structures inside the body of a patient to be examined (which 2D projections or 3D views are reconstructed in the framework of a subsequent image post-processing process) to be reproduced in following monitoring examinations more exactly than has previously been possible.

This object is achieved according to the present invention by an image rendering method for 2D/3D reconstruction and graphical representation of image data of areas to be imaged inside the body of a patient to be examined with the use of a CT-, PET-CT- or MRT-assisted imaging process. According to the invention, all patient-specific examination parameters that were used in the course of a radiological initial examination conducted with computed or magnetic resonance tomography imaging are electronically documented, retrievably and persistently stored, and are automatically reused as a guideline in the framework of at least one CT-, PET-CT or MRT-based follow-up examination conducted for monitoring purposes. For example, this follow-up examination can be a post-operative tumor examination conducted with slice image monitoring in connection with a histological tissue sample extraction (biopsy) occurring in connection under local anesthesia, a CT-assisted or MRT-controlled minimally-invasive intervention implemented for tumor treatment, or a CT-controlled or MRT-controlled operative procedure conducted on a tumor patient for this purpose. The parameter set of the initial examination of the appertaining patient forms a complete patient-specific examination protocol.

According to the invention, all acquisition parameters of an initial examination of the patients as well as all 2D/3D reconstruction parameters and parameters known as "Advanced Presentation States" (i.e. all presentation parameters of slice exposures or reconstructed 2D projections or 3D views of specific tissue regions, internal organs, anatomical subjects or pathological structures (such as tumors, metastases, hematomas, abscesses etc., for example) inside the body of the appertaining patient, the image data of which were acquired in the framework of a radiological follow-up examination implemented with CT-, PET-CT- or MRT-assisted imaging) are among the aforementioned patient-specific examination parameters.

For example, the acquisition parameters that, in the case of a computed tomography follow-up examination of a CT-assisted or PET-CT-assisted initial examination, are to be reused to produce the same or at least similar acquisition conditions in order to be able to compare the image data generated during the two examinations with one another more simply can be, among other things the collimation of the x-ray radiation emitted by an x-ray source, the pitch value to be set, i.e. the ratio of the table feed during a full rotation of the scanning unit (gantry) of a spiral CT apparatus around the longitudinal axis z of the body of the patient lying extended on the examination table of the CT apparatus and the respective acquisition slice thickness, the acceleration voltage and therefore the energy dose (intensity) of the x-ray radiation emitted by an x-ray tube of the CT apparatus for implementation of a scan procedure, the effective mAs value, i.e. the product of the effective amperage of the x-ray tube and the exposure time of an individual slice, and/or the size and position of the scan region to be provided.

Among the 2D projection or 3D reconstruction parameters of the initial examination implemented under CT-assisted or PET-CT-assisted imaging that must be reused as exactly as possible in the framework of the computed tomography follow-up examination in order to be able to compare the image data generated during the two examinations with one another as precisely as possible, may be:

the thickness as well as the axial positions of the individual slices, the convolution seed to be used for CT image reconstruction according to the principle of filtered back-projection by means of inverse radon transformation, the position and width of a rectangular window function that is required for windowing of the displayable greyscale value range in graphical form of digital CT image data to be displayed, and therefore for limitation of the displayable contrast range, the size of the reconstruction region, and/or the spatial orientation (which can be specified with the aid of Cartesian spatial coordinates (x, y and z) and by means of two solid angle coordinates ($\phi$ and $\theta$)) of a 2D or 3D reconstruction of image subjects to be shown, which 2D or 3D reconstruction was generated in the framework of an image post-processing by means of multiplanar reformation (MPR), maximum intensity projection (MIP) or volume rendering technique (VRT).

Multiplanar reformation is an image post-processing method for reconstruction of specific slices proceeding in arbitrary slice planes, which slices are subsequently reconstructed from a number of axial slice images that are combined into one volume data set in order to be able to graphically depict (from better assessment of a pathological tissue change) coronary slices, sagittal slices or slices proceeding in an arbitrary spatial direction in addition to the image data (generated by means of CT-assisted or PET-CT-assisted imaging) of primary acquisition slices proceeding perpendicular to the longitudinal axis z of the body of an examined patient. In maximum intensity projection, those volume elements (voxels) with the respective strongest intensity are projected onto a two-dimensional image plane that is normal relative to the appertaining projection direction for all projection directions. When these 2D projections are considered from various viewing angles, a three-dimensional impression of the tissue regions, organs, anatomical subjects or, respectively, pathological structures is obtained. In the volume rendering technique, a specific density, color and transparency value is associated with each voxel, such that a three-dimensional impression likewise arises upon consideration.

In contrast to this, the acquisition and examination parameters that are to be reused in an MRT-assisted follow-up examination of an initial examination implemented using magnetic resonance tomography imaging to produce acquisition and reconstruction conditions that are the same or at least similar to a high degree in order to be able to compare image data generated during the two examinations with one another more simply are all setting parameters required to implement the radiological imaging process. These setting parameters include, for example: the slice thickness of the individual acquisition slices; the number of the slices to be imaged; as well as all physical MR parameters, such as the field strength $H_0$ of a temporally constant static magnetic field $B_0$ generated by coils, and the angular frequency $W_T$ of a radio-frequency alternating magnetic field $B_T(x, y, t)$ transverse to the static magnetic field $B_0$, this alternating magnetic field $B_T(x, y, t)$ being rotated in the transverse plane $E_{xy}$, and being additionally required to set the atomic nuclei of the hydrogen atoms of tissue cells in specific areas of the inside of the body of a patient to be examined into resonance and thus to excite these hydrogen atoms to process in a non-transient manner. Apart from these setting parameters, those parameters which relate to the spatial orientation of MRT slice images (individual slices), or to the spatial orientation of the individual slices from a number of individual slices merged into volume data sets, must also be re-entered in an MRT-assisted follow-up examination. Moreover, all 2D projection and 3D reconstruction parameters used in the framework of an initial examination implemented using magnetic resonance tomography imaging are to be reused in an MRT follow-up examination, such as, for example, the position (that can be defined by means of Cartesian spatial coordinates (x, y and z)) and the spatial orientation (that can be defined with the use of two solid angle coordinates ($\phi$ and $\theta$)) of a slice exposure (reconstructed by means of multiplanar reformation in the framework of a 2D post-processing) of image subjects to be presented.

Apart from the inventive principle described in the preceding of persistent storage and reuse of acquisition and reconstruction parameters that were set in advance of a radiological initial examination of a patient, according to the invention position data of at least one position marker that establishes the position adopted in the initial examination by the patient on the examination table of a computed tomography or magnetic resonance tomography apparatus used to implement the examination are documented, retrievably and persistently stored in electronic form, and are automatically reused in subsequent CT-, PET-CT- or MRT-based monitoring examinations, or in CT- or MRT-controlled interventional or operative procedures. These position data can be, for example, the Cartesian coordinates $x_0$, $y_0$ and $z_0$ of an established punctiform spot $P(x_0, y_0, z_0)$ on the body surface or inside the body of the patient in a three-dimensional Cartesian coordinate system I (patient coordinate system) relative to the patient which is spanned by the longitudinal axis z of the body and two direction vectors proceeding orthogonal to one another in the x-direction (transverse-horizontal) and in the y-direction (transverse-vertical). These direction vectors are direction vectors of a slice plane $E_{xy}$ normal (transverse) relative to the longitudinal axis z of the body, with a suitably established point A indicating the position of the coordinate origin O in the patient coordinate system. Optionally, the Cartesian coordinates $x_0'$, $y_0'$ and $z_0'$ of a further position marker that designates the position of an established punctiform spot $P'(x_0', y_0', z_0')$ ideally not covered by the patient on the top side of the examination table in a three-dimensional Cartesian coordinate system I' (table coordinate system) relative to the table are stored as position data insofar as the position of the spot P' is not already established anyway by the present position (dependent on the table feed in the ±z-direction) of one of the four corners or the middle position of one of the four edges of the (generally rectangular) examination table. After establishing the positions of both of these points P and P', the patient and table coordinate systems can be set in relation to one another via three position offset coordinates Δx, Δy and Δz as well as via an angle offset coordinate $$\Delta\varphi = 180° + \frac{360°}{\prod [rad]} \cdot \arctan\left[\frac{z_0' - \Delta z + \sqrt{(z_0' - \Delta z)^2 + (x_0' - \Delta x)^2 - x_0^2}}{x_0' - \Delta x + x_0}\right]$$

and be converted into one another with the aid of the following coordinate transformation:

$$\begin{bmatrix} x' \\ y' \\ z' \end{bmatrix} = \begin{pmatrix} \cos(\beta_u \cdot \Delta\varphi) & 0 & \sin(\beta_u \cdot \Delta\varphi) \\ 0 & 1 & 0 \\ -\sin(\beta_u \cdot \Delta\varphi) & 0 & \cos(\beta_u \cdot \Delta\varphi) \end{pmatrix} \cdot \begin{bmatrix} x \\ y \\ z \end{bmatrix} + \begin{bmatrix} \Delta x \\ \Delta y \\ \Delta z \end{bmatrix}.$$

In the above, $$\beta_u := \frac{\prod}{180°} [rad]$$

designates the conversion factor for conversion from degrees into radians. In order to be able to determine the three position offset coordinates Δx, Δy and Δz and the angle offset coordinate Δϕ cited in the preceding, which are required given a CT-assisted or MRT-assisted initial examination and subsequent computed or magnetic resonance tomography monitoring examinations in order to relate table and patient coordinate system to one another, and to convert them into one another via transverse-horizontal, transverse-vertical and/or axial displacement of the patient coordinate system by Δx, Δy and/or Δz in the ±x-, ±y- and ±z-directions as well as possibly via rotation of the patient coordinate system by Δϕ in the ±Δϕ-direction (i.e. via rotation on an axis perpendicular to the x-z-plane of the patient coordinate system parallel to the table plate plane), two position markers that indicate the positions of the point P on the body surface of the patient and of the point P' on the top of the examination table are used as orientation points in the patient and table coordinate systems.

According to the invention, the position marker identifying the position of the patient coordinate system I can be either: a real marker object $M_r$ applied at a fixed, punctiform spot $P(x_0, y_0, z_0)$ on the body surface of the patient, the position of which real marker object $M_r$ being detected in relation to the table coordinate system I' via an optical surface scan of the patient; or a virtual marker object $M_v$ in a 2D topogram generated by means of computed or magnetic resonance tomography imaging, which virtual marker object $M_r$ is positioned at a determined, punctiform spot $P(x_0, y_0, z_0)$ inside the body of the appertaining patient by the radiologist conducting the respective examination.

According to the invention, possible deviations of the position relationship between patient coordinate system and table coordinate system that can occur in two successive radiological examinations conducted using computed or magnetic resonance tomography imaging are detected by comparison of the position of the position marker indicated in relation to the table coordinate system in the surface scans or, respectively, 2D topograms generated in advance of these radiological examinations and compensated in the reconstruction of 2D or 3D views of the areas to be imaged inside the body of the patient, for example using the coordinate transformation specified above. For this purpose, following a radiological follow-up examination a reconstructed 3D view of an area to be imaged inside the body of the patient to be examined (which 3D view was generated from a volume data set of this follow-up examination) undergoes a coordinate transformation with the same position offset and angle offset measures which are required in order to superimpose the two surface scans or, respectively, 2D topograms generated in advance of the two radiological examinations, such that the position marker imaged therein is brought into congruence with itself.

The present invention also concerns a CT-assisted or MRT-assisted image acquisition, image archiving and image rendering system for generation, storage, post-processing, retrieval and graphical visualization of computed or magnetic resonance tomography image data, which system can be used, for example, in the clinical field in the framework of radiological slice image diagnostics as well as in the framework of interventional radiology. Among other things, the system according to the invention has a memory unit in which all acquisition parameters of an initial examination of the patient conducted under CT-, PET-CT- or MRT-assisted radiological imaging; all 2D and 3D reconstruction parameters; and possibly what are known as "Advanced Presentation States" that define presentation parameters of slice exposures or reconstructed 2D projections or 3D views of specific tissue regions, internal organs, anatomical subjects or pathological structures (such as, for example, tumors, metastases, hematomas, abscesses etc.) inside the body of the appertaining patient, are electronically documented and are stored persistently and such that they can be retrieved in order to be able to be automatically reused as a specification for later CT-, PET-CT- or MRT-based follow-up examinations conducted for monitoring purposes or as a specification for subsequent CT-assisted or MRT-controlled interventional or operative procedures. As described above, the parameter set of the initial examination of the appertaining patient forms a complete, patient-specific examination protocol.

Moreover, according to the invention position data of at least one position marker that establishes the position occupied by the patient in the initial examination on the examination table of a computed tomography or magnetic resonance tomography apparatus used to conduct the examination are documented in the aforementioned memory unit, and are stored persistently and such that they can be retrieved in order to be able to be automatically reused in subsequent CT-, PET-CT- or MRT-based monitoring examinations, or CT-controlled or MRT-controlled interventional or operative procedures. As already noted, these position data can be, for example, Cartesian coordinates $x_0$, $y_0$ and $z_0$ of an established punctiform spot $P(x_0, y_0, z_0)$ on the body surface of the patient in a three-dimensional Cartesian coordinate system I (patient coordinate system) relative to the patient, which three-dimensional Cartesian coordinate system I is spanned by the longitudinal axis z of the patient and two direction vectors proceeding orthogonal to one another in the x-direction (transverse-horizontal) and in the y-direction (transverse-vertical). These direction vectors are direction vectors of a slice plane $E_{xy}$ normal (transverse) relative to the longitudinal axis z of the body, with a suitably established point A indicating the position of the coordinate origin O in the patient coordinate system.

The system according to the invention moreover has a data acquisition unit with which deviations of the position relationship between the patient coordinate system I and a three-dimensional Cartesian coordinate system I' relative to the examination table with the coordinate origin O' and the axes x', y' and z' (table coordinate system) orthogonal to one another in pairs are detected in temporally successive radiological examinations conducted under computed or magnetic resonance tomography imaging. The data acquisition unit communicates with the memory unit via a data output interface, such that the spatial coordinates of a position marker detected in the patient coordinate system and table coordinate system detected by the data acquisition unit upon generation of an optical surface scan or 2D topogram (which position marker identifies an established spot on the body surface of the appertaining patient) can be written via the data output interface into a protocol file stored in a memory region of the memory unit.

With the use of an image processing unit integrated into the system according to the invention, these deviations can be compensated in the framework of an image rendering for reconstruction of 2D or 3D views of areas to be imaged in the inside of the body of the patient. For this purpose the 3D view (reconstructed after a follow-up examination) of a tissue region to be examined that was generated from the examination data set of this follow-up examination is rotated in the $\pm\phi$-direction (i.e. around an axis perpendicular to the x-z-plane of the patient coordinate system parallel to the table plate plane) by a specific angle measure which corresponds to the absolute magnitude of the difference between the angle offset measure $\Delta\phi$ between the patient coordinate system and the table coordinate system in the initial examination and the corresponding angle offset measure in the follow-up examination, and/or is shifted in the $\pm x$-, $\pm y$- or $\pm z$-directions by a specific length measure that corresponds to the absolute magnitude of the difference between the length offset measures $\Delta x$, $\Delta y$ and/or $\Delta z$ between the patient coordinate system and the table coordinate system in the initial examination and the appertaining follow-up examination, after the appertaining angle and length measure was calculated by the image processing unit.

The present invention also concerns a computer software product (computer-readable medium encoded with programming instructions) for implementation of the described method upon operation on a screen terminal of the image acquisition, image archiving and image rendering system described in the preceding.

BRIEF DESCRIPTION OF THE DRAWINGS

FIGS. 2a, 2b, 2c and 2d are a flowchart of an embodiment the method according to the invention for reproduction of set examination parameters of a CT-PET-CT- or MRT-assisted initial examination in subsequent radiological monitoring examinations.

DESCRIPTION OF THE PREFERRED EMBODIMENTS

The system components of the image acquisition, image archiving and image rendering system according to the invention and the steps of the associated method according to the invention are described in detail in the following.

Figure 1:
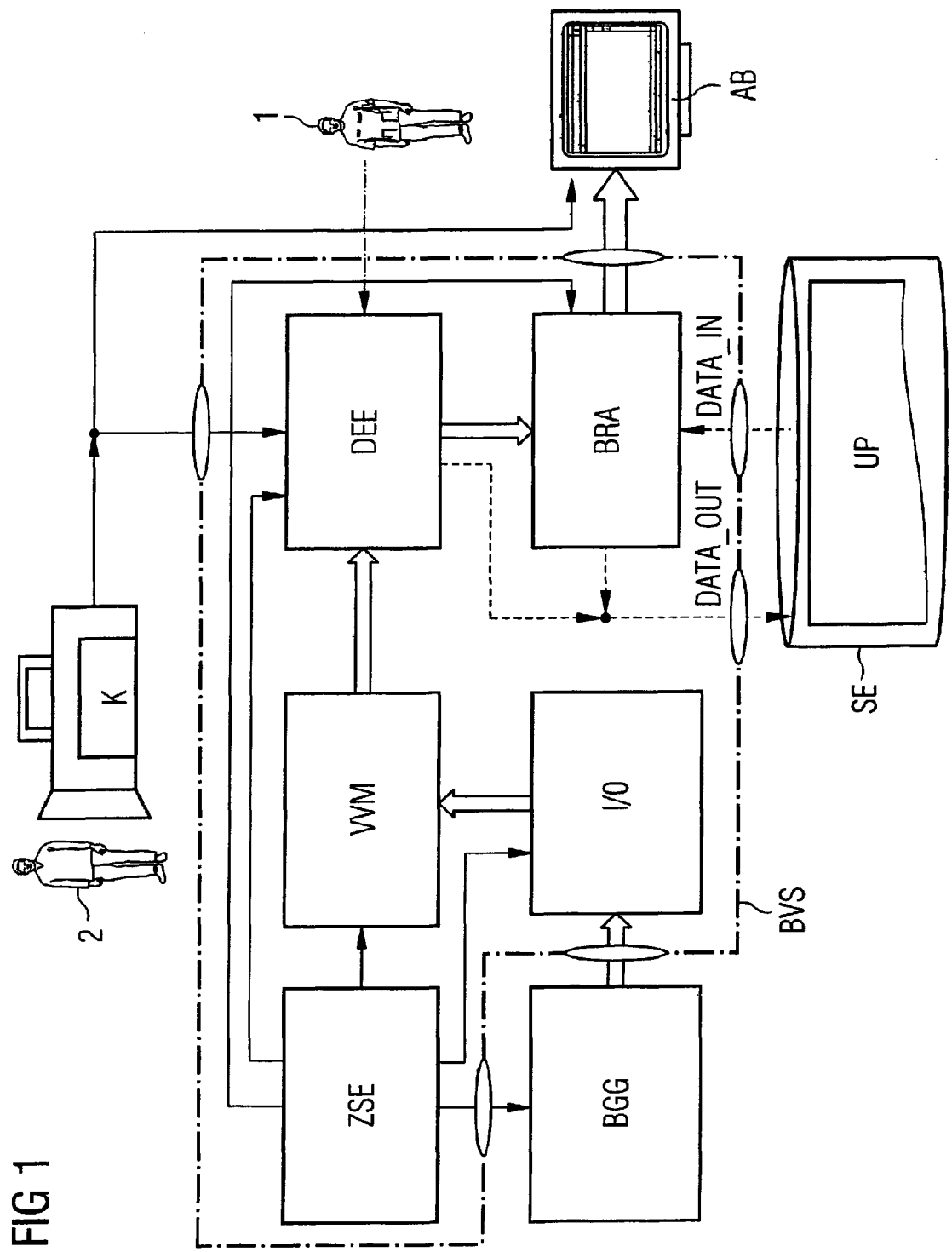
FIG. 1 is a block diagram for illustration of the system architecture of an embodiment of the image acquisition, image archiving and image rendering system according to the invention.
Figure 2A:
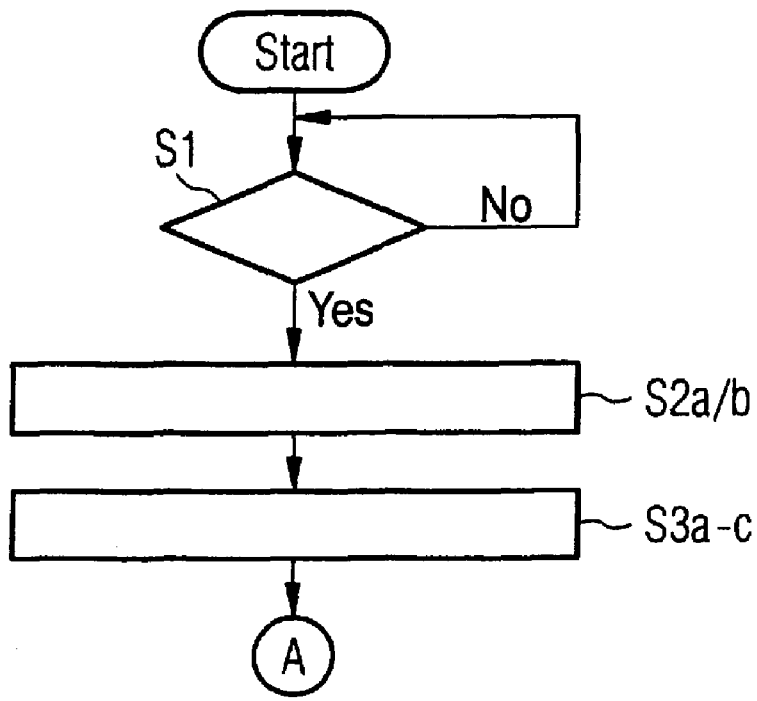
Figure 2B:
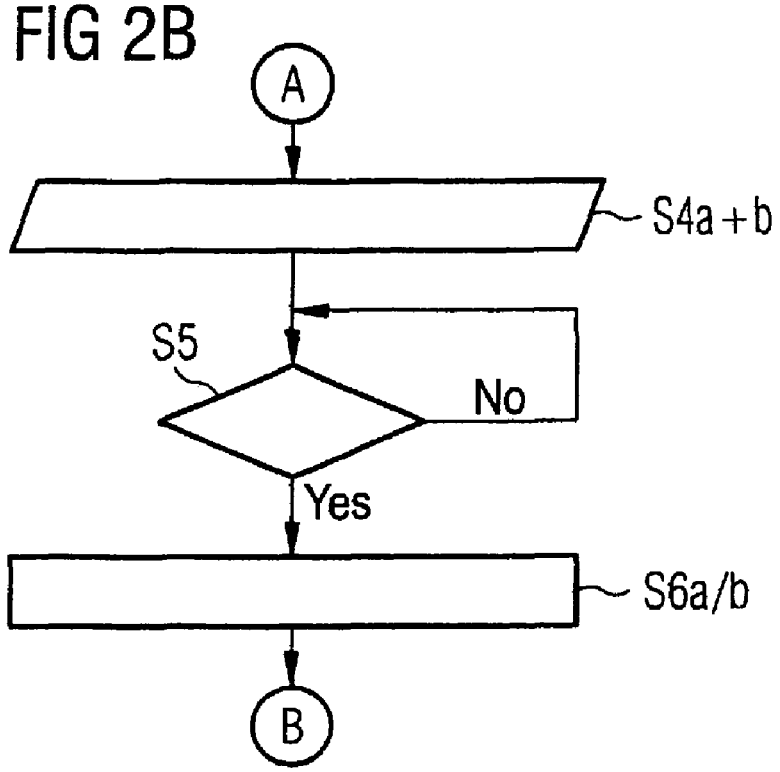

A schematic block diagram of an embodiment of an image acquisition, image archiving and image rendering system according to the present invention is shown in FIG. 1. This system enables image data (generated by a medical technology imaging apparatus BGG (for example by a CT or MRT apparatus)) of tissue regions inside the body of a patient 2 to be examined to be displayed in the form of slice exposures or in the form of reconstructed 2D projections or reconstructed 3D presented from arbitrary projection angles. The image data provided by a computed or magnetic resonance tomography imaging modality are supplied to an image processing system BVS via an input/output interface I/O. In addition to a central processing device ZSE which controls the data exchange with the medical technology imaging apparatus BGG as well as the data exchange between the individual system components of the image processing system BVS, among other things the image processing system BVS includes a pre-processing module VVM with a digital filter for noise suppression, contrast improvement and edge detection. A 2D/3D image rendering module (software application) BRA integrated into the image processing system serves for 2D and/or 3D reconstruction as well as for graphical visualization of the tissue regions to be displayed.

Upon receipt of image data from the medical technology imaging apparatus BGG, depending on the system configuration these can be temporarily or persistently stored in an external image data storage (not shown) after conclusion of the pre-processing in preparation for a later graphical visualization. According to the invention, in the framework of an initial examination of the patient conducted under CT-, PET-CT- or MRT-assisted radiological imaging, all acquisition parameters that were set by a radiologist 1 conducting the examination by manual input into a data acquisition unit DEE of the image processing system BVS as well as all 2D or 3D reconstruction parameters of the image data acquired in the framework of this imaging process, also manually predetermined reconstruction parameters and "Advanced Presentation States" (i.e. presentation parameters of slice exposures or 3D views of specific tissue regions, internal organs, anatomical subjects or pathological structures (such as tumors, metastases, hematomas, abscesses etc., for example) inside the body of an examined patient), are written (initiated by the central control device ZSE) into a patient-specific examination protocol UP of a protocol file in a standardized data format (for example in the DICOM format) via a data output interface DATA_OUT of the image processing system BVS. This protocol file is stored in a memory region of the same or an additional external storage unit SE provided for storage of these parameters. The electronically documented parameters are stored persistently and such that they can be retrieved in order to be able to be automatically reused as a template for later CT, PET-CT- or MRT-based follow-up examinations conducted for monitoring purposes, or as a template for subsequent CT-controlled or MRT-controlled interventional or operative procedures. For this purpose the acquisition and reconstruction parameters set in the framework of the initial examination can be loaded via a data input interface DATA_IN of the image processing system BVS into a local temporary memory of the 2D/3D image rendering application BRA.

As shown in FIG. 1, apart from the aforementioned CT or MRT acquisition parameters and 2D/3D reconstruction parameters, position data of at least one position marker to establish the position occupied by the patient in the initial examination on the examination table of the computed tomography or magnetic resonance tomography apparatus used for implementation of the examination are stored in order to be able to be reused in subsequent CT, PET-CT- or MRT-based monitoring examinations or CT-controlled or MRT-controlled interventional or operative procedures. The position data can be, for example, the Cartesian coordinates $x_0$, $y_0$ and $z_0$ of a fixed, punctiform spot $P(x_0, y_0, z_0)$ on the body surface of the patient in a three-dimensional Cartesian coordinate system I (patient coordinate system) relative to the patient, which coordinate system I is spanned by the longitudinal axis z of the patient and two direction vectors proceeding orthogonal to one another in the x-direction (transverse-horizontal) and in the y-direction (transverse-vertical). These direction vectors are direction vectors of a slice plane $E_{xy}$ normal (transverse) relative to the longitudinal axis z of the body, with a suitably established point A indicating the position of the coordinate origin O in the patient coordinate system.

In order to be able to better compare the image data of the CT-, PET-CT- or MRT-assisted radiological initial examination of the patient with those of a subsequent follow-up examination of the same patient conducted using computed or magnetic resonance tomography imaging, independent of the orientation and position occupied by the patient during the individual examinations on the examination table of the CT or MRT apparatus, deviations of the position relationship between the patient coordinate system I and a three-dimensional Cartesian coordinate system I' related to the examination table with the coordinate origin O' and three orthogonal axes x', y' and z' associated with one another in pairs (table coordinate system) are detected by the aid of the data acquisition unit DEE. For this purpose, the data acquisition unit DEE determines the spatial coordinates of the aforementioned position marker in the presentation region of optical surface scans or abdominothoracic 2D topograms generated with the aid of the CT or MRT apparatus that were generated in advance of the individual examinations, and determines these spatial coordinates relative to the patient coordinate system I and the table coordinate system I'. In the former case, not only the image data acquired by means of CT-, PET-CT- or MRT-assisted imaging and filtered by the pre-processing module VVM, but also the image data acquired by a camera K of an optical surface scan of the patient are supplied the data acquisition unit DEE. The image data are then used by the data acquisition unit DEE to calculate a three-dimensional depiction of the surface contours of the patient and are displayed on the display screen AB of the screen terminal in rendered form as a contour map formed by horizontally and vertically running grid lines equidistant from one another (orthogonal gridding). The aforementioned spatial coordinates (designated as "patient position coordinates" in FIG. 1) are then written via the data output interface DATA_OUT of the image processing system BVS into the patient-specific examination protocol UP of the protocol file stored in the external storage unit SE and there are stored persistently, such that they can be retrieved, just like the aforementioned acquisition and reconstruction parameters. If the patient should be subjected to a further CT-, PET-CT- or MRT-assisted radiological examination after the initial examination, the patient position coordinates stored in the examination protocol UP and related to the respective examinations can be used to compensate deviations (ascribed to different recumbent positions) of the position relationship of patient and table coordinate systems in the initial examination and the follow-up examination in the CT or MRT slice exposures to be presented on the display screen.

These deviations in the 2D or 3D representations of the tissue regions to be examined that are displayed on the display screen AB of the screen terminal can be compensated with the use of the 2D/3D image rendering module BRA integrated into the inventive image processing system, such that the presented image data of the initial examination and the follow-up examination can be better compared with one another, i.e. without taking into account the respective patient position. For example, for this purpose a 3D view (reconstructed following a radiological follow-up examination) of a tissue region to be examined that was generated form the examination data set of this follow-up examination is rotated in the $\pm\phi$-direction (i.e. around an axis perpendicular to the x-z-plane of the patient coordinate system parallel to the table plate plane) by a specific angle measure that corresponds to the absolute magnitude of the difference between the angle offset measure $\Delta\phi$ between the patient coordinate system and the table coordinate system in the initial examination and the corresponding angle offset measure in the follow-up examination; and/or is shifted in the $\pm x$-, $\pm y$- or $\pm z$-directions by a specific length measure which corresponds to the absolute magnitude of the difference between the length offset measures $\Delta x$, $\Delta y$ and/or $\Delta z$ between the patient coordinate system and the table coordinate system in the initial examination and the appertaining follow-up examination after the appertaining angle and length measure was calculated by 2D/3D the image rendering application BRA. After a reconstruction, the central control device ZSE of the image processing system BVS causes the acquired image data to be graphically visualized in two-dimensional and/or three-dimensional form on a display screen AB of a screen terminal.

As already described in part in the preceding, the data acquisition unit DEE and the 2D/3D image rendering application BRA according to the invention are used, among other things, to detect the location of a position marker to identify an established point on the body surface of the patient to be examined, which position marker is displayed in the optical surface scans or 2D topograms of the appertaining patients generated in advance of two CT- or MRT-assisted radiological examinations, and to compensate for the deviation in the position relationships of patient coordinate system and table coordinate system, which deviations are ascribed to a possible different patient positioning in the individual examinations. This can ensue by the two surface scans or 2D topograms generated in advance of the two radiological examinations being superimposed, and the position marker depicted in the two representations is brought into congruence with itself via a coordinate transformation.

There are in principle two alternative possibilities in order to position the position marker (via which the position of the patient coordinate system I is defined relative to the position of the table coordinate system I') at the spot designated by the point P on the body surface of the patient. One option is for the position marker to be directly applied on the skin of the patient to be examined in form of a real marker object $M_r$ which is shown as well in an optical surface scan of the patient. Another option is to generate a position maker: in the form of a virtual marker object $M_v$ displayed on the display screen, which virtual marker object $M_v$ is displayed and positioned in a 2D topogram generated by means of CT, PET-CT or MRT by clicking on this punctiform spot, wherein a marker bit for the pixel corresponding to this point is placed in the associated image data set of this 2D topogram.

In the former case, in each follow-up examination the appertaining real marker object $M_r$ must be applied at the same point on the skin of the patient as in the initial examination. The marker object $M_r$ should thereby be positioned at a point of the body surface that does not shift in the ±y-direction (i.e. transverse-vertical) upon breathing or pulsation movements of the patient lying extended on the examination table of the CT or MRT apparatus. Such a point is located, for example, in the region of the left or right medial clavicle end (extremitas sternalis claviculae) or in the region of the palpable front upper iliac spine (spina iliaca ventralis or spina iliaca anterior superior), a bone projection on the iliac crest (crista iliaca) of the wing of ilium (ala ossis ilii). In the case of a computed tomography examination the marker object $M_r$ should thereby consist of a radio-opaque material that causes no image artifacts, however is easily recognizable on the generated CT images. In the case of a magnetic resonance tomography examination, the marker object $M_r$ should be easy to demarcate in all MRT weightings. The position of the marking object $M_r$ applied on the skin can be detected via a surface scan of the patient both in the case of an implemented CT-assisted or PET-CT-assisted radiological examination and in the case of a radiological examination implemented under MRT imaging. Since the respective position of the examination table is known, the current position and bearing of the patient on the examination table can be determined in relation to this when the two points P and P' are brought into relation with one another by calculation of the position offset and angle offset coordinates of patient coordinate system and table coordinate system. The use of such a real marker object $M_r$ makes it possible for the radiologist to automatically record the orientation and position of the patient on the examination table, such that a surface scan generated in the framework of a prior examination by means of CT-, PET-CT- or MRT-assisted imaging together with additional surface scans that are generated in the framework of later follow-up examinations of this patient (likewise generated by means of computed or magnetic resonance tomography) can be registered without manual input of new bearing or position data. The goal is to cause a marker object $M_r$ applied on the body surface of the patient which is displayed in an optical surface scan generated in advance of an initial examination as well as in an additional optical surface scan of this patient generated in advance of a later follow-up examination to optimally come into congruence with itself given a superimposition of these two contour representations. Insofar as the aforementioned marker object $M_r$ lies within an examination region to be imaged, the radiologist moreover has the possibility to register image data from 3D reconstructions and/or of slices of tissue regions to be presented (which slices are reconstructed at different projection angles) that were calculated from the examination data set of an initial examination together with image data of two-dimensional and/or three-dimensional reconstructed views that were calculated from the examination data set of a follow-up examination without having to make subsequent corrections with regard to the spatial bearing and position of these views for the purpose of better comparability of the examination results of initial examination and follow-up examination.

In the latter case a virtual marker object $M_v$ shown on a display screen is placed at a specific point of an abdominothoracic 2D topogram generated in the framework of a radiological initial examination by means of CT, PET-CT or MRT, and in fact at a point of the body surface that that does not shift in the ±y-direction (i.e. transverse-vertical) upon breathing or pulsation movements of the patient lying extended on the examination table of the CT or MRT apparatus. As already shown, such a point can be found, for example, in the region of the left or right medial clavicle end (i.e. medioclavicular) or in the region of the front upper iliac spine. By using such a virtual marker object $M_v$ it is also made possible for the radiologist to automatically record bearing and position of the patient on the examination table, such that an abdominothoracic 2D topogram generated in the framework of a prior examination by means of CT-, PET-CT- or MRT-assisted imaging together with additional abdominothoracic 2D topograms that are generated in the framework of later follow-up examinations of this patient (likewise implemented by means of computed or magnetic resonance tomography) can be registered without manual input of new bearing or position data. In the event that the marker object $M_v$ lies within an examination region to be imaged, as in the case described above of using a real marker subject the radiologist has the possibility to register image data from 3D reconstructions and/or of slices of tissue regions to be presented (which slices are reconstructed at different projection angles) that were calculated from the examination data set of an initial examination together with image data of two-dimensional and/or three-dimensional reconstructed views that were calculated from the examination data set of a follow-up examination, without having to make subsequent corrections with regard to the spatial bearing and position of these views for the purpose of better comparability of the examination results of initial examination and follow-up examination.

In both cases the marker object $M_r$ or $M_v$ acts as an examination-independent orientation point whose location P describes the location of a fixed point in the patient coordinate system I (such as, for example, the location of its coordinate origin O) and thus permits the establishment of a position relationship of patient coordinate system and table coordinate system via comparison with the position of the point P' on the surface of the examination table which describes the location of a fixed point in the table coordinate system I' (such as, for example, the location of its coordinate origin O'). In this manner it is ensured that image data of 3D reconstructions and/or image data of slices of tissue regions to be presented (which slices are reconstructed from different projection angles) that were calculated from the examination data sets of individual examinations can also be related to the patient coordinate system I as intended. The real marker object $M_r$ applied on the body surface of the patient, like the individual surface scans generated before implementation of the actual radiological examinations of tissue regions of interest with the virtual marker object $M_v$ displayed therein, can also be used to detect the three position offset coordinates $\Delta x$, $\Delta y$ and $\Delta z$ as well as the angle offset coordinates $\Delta \phi$ between patient coordinate system and table coordinate system in a CT-, PET-CT- or MRT-assisted radiological initial examination as well as in further computer or magnetic resonance tomography follow-up examinations of a patient; to establish deviations of the position offset or angle offset coordinates observed in the individual follow-up examinations relative to the position offset or angle offset coordinates in the initial examination, and to possibly compensate these deviations in order to enable a better comparability of the examination results from initial examination and follow-up examination. In order to make this compensation, the 3D view of a tissue region to be examined (which 3D view is reconstructed following a follow-up examination) that was generated from the examination data set of this follow-up examination must be rotated in the ±φ-direction (i.e. around an axis perpendicular to the x-z-plane of the patient coordinate system parallel to the table plate plane) by a specific angle measure which corresponds to the absolute magnitude of the difference between the angle offset measure Δφ between the patient coordinate system and the table coordinate system in the initial examination and the corresponding angle offset measure in the follow-up examination, and/or is shifted in the ±x-, ±y- or ±z-directions by a specific length measure that corresponds to the absolute magnitude of the difference between the length offset measures Δx, Δy and/or Δz between patient coordinate system and table coordinate system in the initial examination and the appertaining follow-up examination. The detection and correction of the deviations can thereby ensue automatically with the aid of an image processing system. After the position offset and angle offset coordinates detected in the individual examinations have been compared with one another, the image data of the follow-up examination can be registered together with the image data of the initial examination, i.e. be stored in a common file.

In FIGS. 2a through 2d the method according to the invention is presented in detail in the form of a workflow consisting of four parts. In planning (S1) a CT-, PET-CT- or, respectively, MRT-assisted radiological initial examination of a patient, an optical surface scan of the patient to be examined is initially generated (S2a) after placement of a position marker $M_r$ or, respectively, $M_v$ indicating the location of a fixed point in the patient coordinate system I at an established spot of the body surface of the patient, or a 2D topogram of tissue regions, organs, anatomical subjects or pathological structures inside the body of the patient to be examined is generated (S2b) by means of computed or magnetic resonance tomography imaging. In this 2D topogram, the appertaining position marker $M_r$ or $M_v$ is placed at an established point within the area depicted in this 2D representation. Following this the CT-, PET-CT or MRT-assisted radiological initial examination is conducted (S3a) using specific CT/MRT acquisition parameters and reconstructed 3D views or, respectively, 2D views presented from new projection angles of the appertaining area are calculated (S3b) using specific reconstruction parameters, whereupon slice exposures generated in the framework of this initial examination and/or 2D/3D reconstructions calculated with regard to the image data of these slice exposures are displayed (S3c) on the display screen AB of a screen terminal. The recorded CT or, respectively, MRT acquisition parameters, patient position coordinates and 2D/3D reconstruction parameters are then written (S4a) into a patient-specific examination protocol that is stored (S4b) in a protocol file.

If the implementation of a computed or magnetic resonance tomography follow-up examination of the patient should be planned (S5) following the CT-, PET-CT- or MRT-assisted radiological initial examination, a further optical surface scan of the patient to be examined is initially generated (S6a) after placement of a position marker $M_r$ or, respectively, $M_v$ (indicating the location of a fixed point in the patient coordinate system) on the established spot of the body surface of the patient, or a further 2D topogram is generated (S6b) by means of computed or magnetic resonance tomography imaging of the tissue regions, organs, anatomical subjects or pathological structures inside the body of the patient to be examined in which the appertaining position marker $M_r$ or, respectively, $M_v$ is then placed at an established spot within the area depicted in this 2D representation. According to the invention, the CT/MRT acquisition parameters, patient position coordinates and 2D/3D reconstruction parameters detected in the course of the initial examination are thereupon loaded (S7a) from the patient-specific examination protocol UP (stored in the protocol file) of the initial examination and read (S7b). After detection (S8) of a possible deviation of the position relationships of patient coordinate system I and table coordinate system I' by comparison of the position of aforementioned position marker $M_r$ or $M_v$ in the optical surface scans or 2D topograms of the patient generated in advance of the initial examination and follow-up examination, the CT-, PET-CT- or MRT-assisted radiological follow-up examination is then conducted (S9a) using the CT/MRT acquisition parameters read from the patient-specific protocol UP of the initial examination, and reconstructed 3D views or 2D views presented from new projection angles of the appertaining area are calculated (S9b). The reconstruction parameters loaded from the patient-specific examination protocol UP of the initial examination are used for this purpose. In a further step (S10) the deviation (detected in step S8 and caused by different patient position in the initial examination and follow-up examination) of the position relationship of patient coordinate system I and table coordinate system I' is then compensated in the two radiological examinations conducted under CT-, PET-CT- or MRT-assisted imaging, whereupon the slice exposures generated in the framework of the follow-up examination and/or the 2D/3D reconstructions calculated with regard to the image data of these slice exposures are displayed (S11) on the display screen AB of the screen terminal.

A number of advantages result from the features of the inventive method described in the preceding. The orientation and position of a patient to be examined by means of computed or magnetic resonance tomography imaging are automatically detected by an optical surface scan or an abdominothoracic 2D topogram. This has the result that the time-consuming manual input of bearing and position data that describe the bearing of the patient coordinate system (which bearing is different under the circumstances from examination to examination) in relation to the coordinate system of the examination table on which the patient is located in extended position during the respective examination is foregone given the registration of the individual examination data sets of the appertaining patient. Since deviations of the position offset or angle offset coordinates of patient coordinate system and table coordinate system that are to be observed in a CT-, PET-CT- or MRT-assisted follow-up examination of the patient relative to the corresponding position offset or, respectively, angle offset coordinates in a computer or magnetic resonance tomography initial examination can be automatically detected and possibly also automatically compensated, the image data acquired in the framework of the initial examination can be exactly reproduced even given different patient positions during the individual examinations.

Moreover, as a result of the method according to the invention the possibility exists to automatically derive examination results of a conducted CT-, PET-CT- or MRT-assisted follow-up examination of a patient from examination results of a previous initial examination of this patient conducted using a computed or magnetic resonance tomography imaging method, in that a patient-specific examination protocol UP is used as a basis in which the acquisition and reconstruction parameters of the initial examination (and, in the case of scan and/or reconstruction parameters deviating from these in a follow-up examination, these parameters as well) are stored persistently and such that they can be retrieved. The method according to the invention therefore offers a radiologist an exact comparison capability of the image data of initial examination and follow-up examination. An additional diagnostic safety for the patient is thereby achieved since, for example, a region of a tumor tissue that was diagnosed in the framework of an initial examination of the patient conducted under radiological imaging is also imaged with the same acquisition and reconstruction parameters in a conducted CT-, PET-CT- or MRT-assisted follow-up examination of the patient in advance of a later tumor operation, and therefore in the same position and orientation in a reconstructed 2D projection or, respectively, 3D view as in the radiological initial examination.

The workflow of the follow-up examination is significantly improved and simplified by this since all acquisition and reconstruction parameters required for implementation of the examination do not have to first be compiled from different data sources and manually input, as has previously been typical in every follow-up examination; rather, said acquisition and reconstruction parameters are stored in a common protocol file and therefore are available via a single data access. CT-, PET-CT- or MRT-assisted follow-up examinations of a computer or magnetic resonance tomography initial examination of a patient can thus be planned and conducted without significant effort. The time expenditure required for the image post-processing is also significantly shortened by the method according to the invention since, given the graphical presentation of the image data of an examination data set acquired in the framework of the follow-up examination, a redefinition of the presentation parameters of slice exposures and reconstructed 2D projections or, respectively, 3D views that were used to present the image data of an examination data set acquired in the framework of the initial examination is foregone by using stored "Advanced Presentation States".

From the preceding statements it follows that an adaptation of the standard examination protocol used for planning the initial examination before conducting a follow-up examination is no longer necessary given use of the method according to the invention, and the time expenditure required for this is foregone.

The method described in the preceding according to the invention thus offers space for manifold application possibilities, in particular in the field of oncology.

Although modifications and changes may be suggested by those skilled in the art, it is the intention of the inventors to embody within the patent warranted hereon all changes and modifications as reasonably and properly come within the scope of their contribution to the art.

We claim as our invention:

1. An image rendering method for multi-dimensional reconstruction and graphical representation of image data representing an interior of the body of a patient, said method comprising the steps of:

obtaining image data of the interior of the body of a patient in a radiological initial examination using an initial imaging modality selected from the group consisting of computed tomography and magnetic resonance tomography, using patient-specific examination parameters to implement a procedure to acquire image data from the interior of the body of the patient with said initial imaging modality and to generate an image of the interior of the body of the patient, said patient-specific examination parameters allowing a supplicated repetition of said procedure;

persistently electronically storing said patient-specific examination parameters; and electronically retrieving the persistently electronically stored examination parameters and using the retrieved parameters to implement a duplicate of said procedure including generation of a follow-up image of the interior of the patient, in an imaging modality-assisted follow-up examination selected from the group consisting of computed tomography-assisted follow-up examinations, positron emission tomography-computed tomography-assisted follow-up examinations, and magnetic resonance tomography-assisted follow-up examinations.

2. A method as claimed in claim 1 comprising employing patient-specific examination parameters comprising data acquisition parameters that set said initial imaging modality to acquire said image data in said procedure and that set an imaging modality for implementing said procedure in said imaging modality-assisted follow-up examination.

3. A method as claimed in claim 1 comprising selecting said patient-specific examination parameters from the group consisting of reconstruction parameters for presentation of a reconstructed 2D projection of a tissue region in the patient, reconstruction parameters for presentation of a reconstructed 2D projection of an internal organ in the patient, reconstruction parameters for presentation of a reconstructed 2D projection of an anatomical subject in the patient, reconstruction parameters for presentation of a reconstructed 2D projection of a pathological structure in the patient, reconstruction parameters for reconstruction of a reconstructed 3D view of a tissue region in the patient, reconstruction parameters for presentation of a reconstructed 3D view of an internal organ in the patient, reconstruction parameters for presentation of a reconstructed 3D view of an anatomical subject in the patient, and reconstruction parameters for presentation of a reconstructed 3D view of a pathological structure in the patient.

4. A method as claimed in claim 1 comprising employing, as said patient-specific examination parameters, position data that establish a position occupied by the patient on an examination table of the initial imaging modality.

5. A method as claimed in claim 4 comprising employing, as said position data, Cartesian coordinates of a position marker at an established punctiform location selected from the group consisting of on the body surface of the patient and inside the body of the patient, in a three-dimensional patient coordinate system represented as a three-dimensional Cartesian coordinate system wherein a longitudinal axis of the body of the patient corresponds to the z-direction of the Cartesian coordinate system, and comprising two direction vectors proceeding orthogonally to each other respectively in the x-direction and the y-direction of the Cartesian coordinate system, said direction vectors defining a slice plane that is normal to the longitudinal axis of the body, and said Cartesian coordinate system having an established point indicating the position of the coordinate origin of the patient coordinate system.

6. A method as claimed in claim 5 comprising employing a real marker object as said position marker and applying said real marker object on the body surface of the patient at said punctiform location, and detecting said real marker object by implementing an optical surface scan of the patient in relation to a further three-dimensional Cartesian coordinate system defining the position of the examination table.

7. A method as claimed in claim 5 comprising employing, as said position marker, a virtual marker object located at said punctiform location inside the body of the patient in a 2D topogram generated by said initial imaging modality.

8. A method as claimed in claim 5 comprising identifying a deviation in a position relationship between the patient coordinate system and a further three-dimensional Cartesian coordinate system for an examination table employed in said imaging modality-assisted follow-up examination by comparing a position of the position marker relative to said further three-dimensional coordinate system in respective scans of the patient implemented in advance of said initial examination and in advance of said imaging modality-assisted follow-up examination.

9. A method as claimed in claim 8 comprising reconstructing a multi-dimensional view of the interior of the body of the patient from image data acquired in said imaging modality-assisted follow-up examination and, when reconstructing said multi-dimensional view, compensating for said deviation of the position relationship.

10. A method as claimed in claim 9 comprising compensating for said deviation when reconstructing said multi-dimensional view by subjecting said image data acquired in said imaging modality-assisted follow-up examination to a coordinate transformation comprising position offsets and angle offsets that cause said position marker to be superimposed in the respective scans implemented before said initial examination and before said imaging modality-assisted follow-up examination.

11. A method as claimed in claim 10 comprising implementing said coordinate transformation by rotating a three-dimensional view, reconstructed from the image data acquired in said imaging modality-assisted follow-up examination, in the plane of the examination table by an angle corresponding to an absolute magnitude of a difference between an angle offset between said patient coordinate system and said table coordinate system in the initial examination and a corresponding angle offset in said imaging modality-assisted follow-up examination, and/or shifting said 3D view positively or negatively in any of said x-direction, said y-direction or said z-direction by a length corresponding to an absolute magnitude of a difference between the length offset between said patient coordinate system and said table coordinate system in the initial examination and the imaging modality-assisted follow-up examination, after said angle offset and said length offset is calculated by identifying a difference of the position data of the position marker in the respective scans implemented before said initial examination and before said follow-up examination.

12. A method as claimed in claim 1 comprising, during said initial examination:
acquiring patient position coordinates by implementing a scan of the patient selected from the group consisting of an optical scan of the patient after placement of a position marker at a fixed point on the body surface of the patient in a patient coordinate system, and generating a 2D topogram of an internal region in the body of the patient by computed tomography or magnetic resonance tomography in which a position marker is located at an established point within said region;
acquiring image data by operating said initial imaging modality with acquisition parameters, electronically calculating a reconstructive multi dimensional view of the interior of the patient using reconstruction parameters, and displaying said multi-dimensional view at a display screen of a display terminal; and
electronically entering said patient position coordinates, said acquisition parameters and said reconstruction parameters into a patient-specific examination protocol for said initial examination, and electronically storing said protocol in a protocol file.

13. A method as claimed in claim 12 comprising, in said imaging modality-assisted follow-up examination:
implementing a further scan of the patient to identify coordinates of said position marker at the patient at a time of said imaging modality-assisted follow-up examination, to identify patient position coordinates of the patient for said imaging modality-assisted follow-up examination;
electronically reading said acquisition parameters, said patient position coordinates and said reconstruction parameters from said protocol file for said initial examination;
comparing the position of the position marker from the protocol file and the position of the position marker at said time of said imaging modality- assisted follow-up examination to detect deviation in a position relationship between a patient coordinate system and a table coordinate system;
implementing said imaging modality-assisted follow-up examination using said acquisition parameters from said protocol file, to acquire follow-up image data, calculating a follow-up reconstructed multi-dimensional view of the region of the patient from said follow-up image data using said reconstruction parameters from said protocol file;
when reconstructing said follow-up multi-dimensional view, compensating for said deviation in said position relationship, to obtain a position relationship-compensated follow-up image; and
displaying said position relationship-compensated follow-up image at a display screen.

14. An imaging system for multi-dimensional reconstruction and graphical representation of image data representing an interior of the body of a patient, said method comprising:
an initial imaging modality that generates an image of the interior of the body of a patient in a radiological initial examination, said initial imaging modality being selected from the group consisting of computed tomography and magnetic resonance tomography, said initial examination modality using patient-specific examination parameters implement a procedure to acquire image data from the interior of the body of the patient with said initial imaging modality and to generate an image of the interior of the body of the patient, said patient-specific examination parameters allowing a supplicated repetition of said procedure;
a memory that persistently stores said patient-specific examination parameters; and
a follow-up imaging modality that electronically retrieves the persistently electronically stored examination parameters and uses the retrieved parameters to implement a duplicate of said procedure including generation of a follow-up image of the interior of the patient, in an imaging modality-assisted follow-up examination selected from the group consisting of computed tomography-assisted follow-up examinations, positron emission tomography-computed tomography-assisted follow-up examinations, and magnetic resonance tomography-assisted follow-up examinations.

15. An imaging system as claimed in claim 14 wherein said follow-up imaging modality employs patient-specific examination parameters comprising data acquisition parameters that set said initial imaging modality to acquire said image data in said procedure and that set an imaging modality for implementing said procedure in said imaging modality-assisted follow-up examination.

16. An imaging system as claimed in claim 14 wherein said follow-up imaging modality said patient-specific examination parameters selected from the group consisting of reconstruction parameters for presentation of a reconstructed 2D projection of a tissue region in the patient, reconstruction parameters for presentation of a reconstructed 2D projection of an internal organ in the patient, reconstruction parameters for presentation of a reconstructed 2D projection of an anatomical subject in the patient, reconstruction parameters for presentation of a reconstructed 2D projection of a pathological structure in the patient, reconstruction parameters for reconstruction of a reconstructed 3D view of a tissue region in the patient, reconstruction parameters for presentation of a reconstructed 3D view of an internal organ in the patient, reconstruction parameters for presentation of a reconstructed 3D view of an anatomical subject in the patient, and reconstruction parameters for presentation of a reconstructed 3D view of a pathological structure in the patient.

17. An imaging system as claimed in claim 14 wherein said follow-up imaging modality employs, as said patient-specific examination parameters, position data that establish a position occupied by the patient on an examination table of the initial imaging modality.

18. An imaging system as claimed in claim 17 wherein said follow-up imaging modality employs, as said position data, Cartesian coordinates of a position marker at an established punctiform location selected from the group consisting of on the body surface of the patient and inside the body of the patient, in a three-dimensional patient coordinate system represented as a three-dimensional Cartesian coordinate system wherein a longitudinal axis of the body of the patient corresponds to the z-direction of the Cartesian coordinate system, and comprising two direction vectors proceeding orthogonally to each other respectively in the x-direction and the y-direction of the Cartesian coordinate system, said direction vectors defining a slice plane that is normal to the longitudinal axis of the body, and said Cartesian coordinate system having an established point indicating the position of the coordinate origin of the patient coordinate system.

19. An imaging system as claimed in claim 18 wherein said follow-up imaging modality employs a real marker object as said position marker, said real marker object being applied on the body surface of the patient at said punctiform location, and said follow-up imaging modality detecting said real marker object by implementing an optical surface scan of the patient in relation to a further three-dimensional Cartesian coordinate system defining the position of the examination table.

20. An imaging system as claimed in claim 18 wherein said follow-up imaging modality employs, as said position marker, a virtual marker object located at said punctiform location inside the body of the patient in a 2D topogram generated by said initial imaging modality.

21. An imaging system as claimed in claim 18 comprising a process configured to identify a deviation in a position relationship between the patient coordinate system and a further three-dimensional Cartesian coordinate system for an examination table employed in said imaging modality-assisted follow-up examination by comparing a position of the position marker relative to said further three-dimensional coordinate system in a scan of the patient implemented in advance of said imaging modality-assisted follow-up examination.

22. An imaging system as claimed in claim 21 comprising an image computer configured to reconstruct a multi-dimensional view of the interior of the body of the patient from image data acquired in said imaging modality-assisted follow-up examination that, when reconstructing said multi-dimensional view, compensates for said deviation of the position relationship.

23. An imaging system as claimed in claim 22 wherein said image computer is configured to compensate for said deviation when reconstructing said multi-dimensional view by subjecting said image data acquired in said imaging modality-assisted follow-up examination to a coordinate transformation comprising position offsets and angle offsets that cause said position marker to be superimposed in the respective scans implemented before said initial examination and before said imaging modality-assisted follow-up examination.

24. An imaging system as claimed in claim 23 wherein said image computer is configured to implement said coordinate transformation by rotating a three-dimensional view, reconstructed from the image data acquired in said imaging modality-assisted follow-up examination, in the plane of the examination table by an angle corresponding to an absolute magnitude of a difference between an angle offset between said patient coordinate system and said table coordinate system in the initial examination and a corresponding angle offset in said imaging modality-assisted follow-up examination, and/or shifting said 3D view positively or negatively in any of said x-direction, said y-direction or said z-direction by a length corresponding to an absolute magnitude of a difference between the length offset between said patient coordinate system and said table coordinate system in the initial examination and the imaging modality-assisted follow-up examination, after said angle offset and said length offset is calculated by identifying a difference of the position data of the position marker in the respective scans implemented before said initial examination and before said follow-up examination.

25. An imaging system as claimed in claim 14 wherein said initial modality during said initial examination:
  acquires patient position coordinates by implementing a scan of the patient selected from the group consisting of an optical scan of the patient after placement of a position marker at a fixed point on the body surface of the patient in a patient coordinate system, and generates a 2D topogram of an internal region in the body of the patient by computed tomography or magnetic resonance tomography in which a position marker is located at an established point within said region;
  acquires image data by operating said initial imaging modality with acquisition parameters, electronically calculating a reconstructive multi-dimensional view of the interior of the patient using reconstruction parameters, and displaying said multi-dimensional view at a display screen of a display terminal; and
  electronically enters said patient position coordinates, said acquisition parameters and said reconstruction parameters into a patient-specific examination protocol for said initial examination, and electronically stores said protocol in a protocol file.

26. An imaging system as claimed in claim 25 wherein said follow-up imaging modality, in said imaging modality-assisted follow-up examination:
  implements a further scan of the patient to identify coordinates of said position marker at the patient at a time of said imaging modality-assisted follow-up examination, to identify patient position coordinates of the patient for said imaging modality-assisted follow-up examination;

electronically reads said acquisition parameters, said patient position coordinates and said reconstruction parameters from said protocol file for said initial examination;

compares the position of the position marker from the protocol file and the position of the position marker at said time of said imaging modality-assisted follow-up examination to detect deviation in a position relationship between a patient coordinate system and a table coordinate system;

implements said imaging modality-assisted follow-up examination using said acquisition parameters from said protocol file, to acquire follow-up image data, calculating a follow-up reconstructed multi-dimensional view of the region of the patient from said follow-up image data using said reconstruction parameters from said protocol file;

when reconstructing said follow-up multi-dimensional view, compensates for said deviation in said position relationship, to obtain a position relationship-compensated follow-up image; and displays said position relationship-compensated follow-up image at a display screen.

27. A non-transitory computer-readable storage medium encoded with programming instructions for operating an imaging system for multi-dimensional reconstruction and graphical representation of image data representing an interior of the body of a patient, said programming instructions causing said system to:

generate an image of the interior of the body of a patient in a radiological initial examination using an initial imaging modality selected from the group consisting of computed tomography and magnetic resonance tomography, using patient-specific examination parameters to implement a procedure to acquire image data from the interior of the body of the patient with said initial imaging modality and to generate an image of the interior of the body of the patient, said patient-specific examination parameters allowing a supplicated repetition of said procedure;

persistently electronically store said patient-specific examination parameters; and electronically retrieve the persistently electronically stored examination parameters and use the retrieved parameters to implement a duplicate of said procedure including generation of a follow-up image of the interior of the patient, in an imaging modality-assisted follow-up examination selected from the group consisting of computed tomography-assisted follow-up examinations, positron emission tomography-computed tomography-assisted follow-up examinations, and magnetic resonance tomography-assisted follow-up examinations.

* * * * *